United States Patent [19]
Reese

[11] Patent Number: 4,723,541
[45] Date of Patent: Feb. 9, 1988

[54] BONE SCREW AND METHOD

[76] Inventor: Hewitt W. Reese, 3214 S. River, Tempe, Ariz. 85282

[21] Appl. No.: 864,415

[22] Filed: May 19, 1986

[51] Int. Cl.⁴ .................................................. A61F 5/04
[52] U.S. Cl. .............................. 128/92 YF; 128/92 YE; 128/92 YZ
[58] Field of Search .......... 128/92 YF, 92 YE, 92 YZ

[56] References Cited

U.S. PATENT DOCUMENTS

| | | | |
|---|---|---|---|
| 3,499,222 | 3/1970 | Linkow et al. | 128/92 YF |
| 3,809,075 | 5/1974 | Matles | 128/92 YF |
| 4,016,874 | 4/1977 | Maffei et al. | 128/92 YZ |
| 4,059,102 | 11/1977 | Devas | 128/92 YF |
| 4,175,555 | 11/1979 | Herbert | 128/92 YF |
| 4,456,005 | 6/1984 | Lichty | 128/92 YF |
| 4,463,753 | 8/1984 | Gustilo | 128/92 YF |
| 4,640,271 | 2/1987 | Lower | 128/92 YF |

Primary Examiner—C. Fred Rosenbaum
Assistant Examiner—Jerome R. Smith, Jr.
Attorney, Agent, or Firm—Harry M. Weiss & Associates

[57] ABSTRACT

A bone screw for use in joining the fractured sections of the phalanx and a method for its use are disclosed. The bone screw includes a smooth cylindrical central shaft with coarse threads at each end of the shaft. The threads can be a greater diameter than the diameter of the shaft with the threads at each end have substantially the same pitch. The threads at the two ends of the central shaft are of opposite hand; that is, the threads at one end are right handed while those at the opposite end are left handed. In one embodiment, one end of the bone screw is provided with a screw slot which will accept a screw-driving tool for inserting the screw.

6 Claims, 6 Drawing Figures

BONE SCREW AND METHOD

BACKGROUND OF THE INVENTION

This invention relates generally to a bone screw and method for its use, and more specifically to a bone screw and method for joining the fractured sections of a phalanx or the like.

In the fixation of fractured bone sections, a supporting member is often implanted into the fractured sections to stabilize those sections until these sections have had an opportunity to mend. With the phalanges, that is the bones of the fingers and toes, the supporting structure often takes the form of a pin which is inserted through the fractured section. The phalanges are generally hollow tube-like structure of boning material and a hole is bored through the center of the tubes and a metallic pin is inserted into this hole to keep the fractured segments aligned. The use of a pin, however, does not force the fractured sections together, but merely keeps them aligned along a central axis. To force the fractured sections of the bone together, a screw is often inserted into the bone sections to draw them together as well as to maintain axial alignment.

Bone screws take many forms. In one form the bone screw takes a "nut and bolt" form in which the bolt is inserted through a hole through two bone sections and the sections are drawn together by a nut which is threaded onto the bolt with the nut external to the bone sections. Such a bone screw is not applicable, however, to fractures of the phalanges.

In another form, as illustrated in U.S. Pat. No. 4,059,102, the bone screw is form in which the lading and trailing end portions of the screw have different diameters as well as opposite handed threads. The use of such a bone screw requires the drilling of a fairly large sized pilot hole to accommodate the end of the screw having the larger diameter. the large pilot hole adds to the trauma of the injury and is therefore an impediment to rapid recovery. If the diameter of the large sized end portion is made small to minimize the necessary pilot hole, the smaller end is necessarily too small of a diameater to have good holding power within the generally hollow phalanx.

In another form of bone screw is illustrated, for example, in U.S. Pat. No. 4,175,555, the bone screw is provided with screw threads which are like handed on each end, but are of a different pitch on the opposite ends of the screw. The use of such a screw requires the insertion of the screw along its total length. That is, the entire length of the screw must be threaded through a first one of the fractured sections and then into the other fractured section. During the insertion of the screw through its entire length, first set of threads is traumatizing the interior of the bone sections and then the other set of screws of different pitch, is further traumatizing at least one of the sections.

In view of the foregoing difficulties of supporting instruments for use in aiding the healing of fractured bones, a need existed for an improved bone screw and method for its use which would securely hold the fractured sections of bone together during healing without adding an undue amount of trauma.

It is therefore an object of this invention to provide an improved bone screw for joining fractured sections of a phalanx.

It is another object of this invention to provide an improved method for joining fracture sections of a phalanx.

It is yet another object of this invention to provide an improved bone screw and method for its use in joining fractured bone sections which provides for compressibly holding the bone segments without traumatizing the injured bone.

SUMMARY OF THE INVENTION

The foregoing and other objects and advantages the invention are achieved through the use of a bone screw which can be easily inserted into the fractured sections of a phalanx or the like. In one embodiment, the bone screw includes a smooth cylindrical shaft having coarse threads at each ends of the shaft. The threads have a greater diameter than the diameter of the shaft and the threads at each end have substantially the same diameter and the same pitch; although, the diameters of the threads need not always be the same. The threads at one end of the screw are of opposite hand from the threads of the other end. A screw slot or other means are provided on one end of the shaft to accept a tool for the rotation insertion of the screw.

The foregoing and other objects, features and advantages of this invention will be apparaent from the following, more particular description of the preferred embodiments of this invention, as illustrated in the accompanying drawings.

DETAILED DESCRIPTION OF THE PREFERRED EMBODIMENTS

Figure 1:
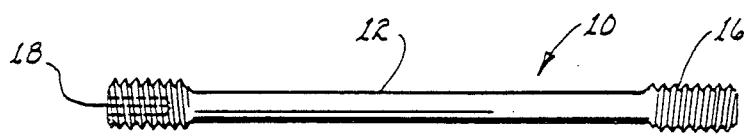
FIG. 1 illustrates a bone screw in accordance with the invention.

FIG. 1 schematically illustrates a bone screw 10 in accordance with the invention. The bone screw includes a central, generally smooth, cylindrical shaft 12. At each end of the central shaft is a set of threads 14, 16 as illustrated. Threads 14 are right handed while threads 16 are left handed. Although the right handed and left handed threads can be reversed, from end to end, it is important that the threads at the opposite ends of shaft 12 be opposite handed. Threads 14 and 16, although only indicted schematically in this view, are self tapping threads so that when they are inserted into a pilot hole they will cut their own threads. The pilot hole does not need to be threaded. Threads 14 and 16 are each of the same diameter and each are of greater diameter than the smooth cylindrical shaft 12; although, the diameter of the threads 14 and 16 need not always be the same. In addition, threads 14 and 16 have the same pitch, or number of threads per millimeter of length. in a preferred embodiment of the invention, threads 14 and 16 are widely spaced so that as the thread is advanced into a bone section the screw advances rapidly with little damage to the inside of the bone. One end of the bone screw includes a slot 18 or other means into which a tool can be inserted to impart rotation to the screw.

The bone screw, in accordance with the invention, is provided in a variety of sizes to be used with fractures of different phalanges or the like and with bones of different sizes. In addition, the screw slot 18, hexaganol female opening to accommodate a hexaganol wrench, or the like is provided at one end of the screw. The screw is preferably made of surgical stainless steel or the like, but can also be made, for example, of plastic or the like to reduce the weight of the screw.

Figure 2:
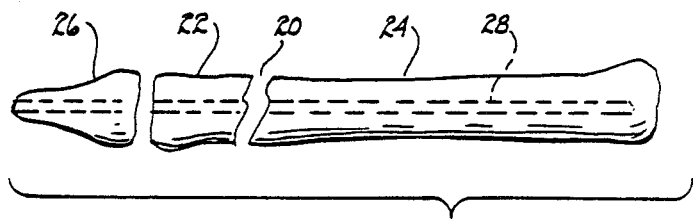
FIGS. 2-6 illustrate steps for joining fractured bone segments, in accordance with the invention.

FIGS. 2-6 illustrate a method by which fractured bone segments or sections can be joined using the bone screw, in accordance with the invention, to aid in the fixation of the bone segments. FIG. 2 illustrates schematically the repair of a fracture phalanx. The invention is specifically formulated for the repair of fractures of the fingers or toes, and is here illustrated showing the repair of a fractured toe. As illustrated, a fracture 20 between sections 22 and 24 of the phalanx is to be repaired. Phalanx 26 is located at the extremity of the toe. As is done when a pin is to be inserted to repair a fracture, a hole 28 is bored through bones 26 and the fractured sections 22 and 24 along the axis of the generally elongated bones. The hole is bored through the generally hollow central portion of the bones leaving the bone cylinder intact.

Figure 3:
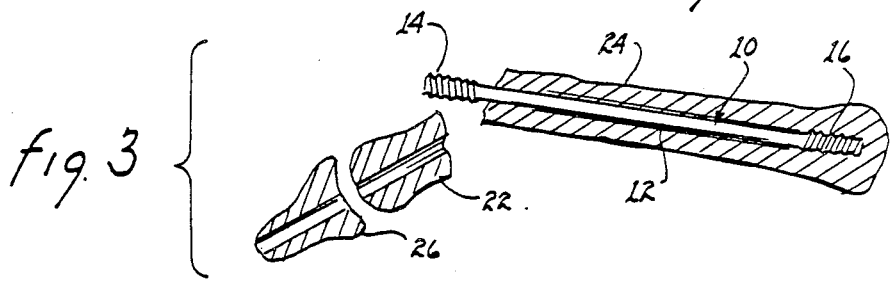

As illustrated schematically in FIG. 3, bone 26 and fractured section 22 are displaced away from the axis running through the bones so that a screw 10 can be inserted into the pilot hole along the axis of fractured segment 24. The bone screw 10 is inserted by rotating the screw using a screwdriving tool (not shown) and relying upon the threads 16 at the leading end of screw 10 to tap threads along pilot hole 28. The screw is advanced into fractured section 24 so that the majority of the smooth cylindrical shaft 12 of screw 10 is positioned within fractured segment 24 and only threads 14 at the trailing end of the screw extend out of section 24.

Figure 4:
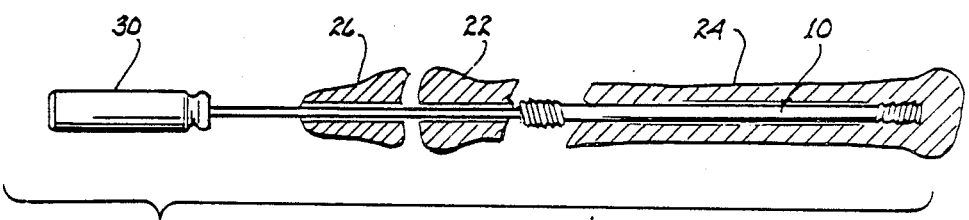
Figure 5:
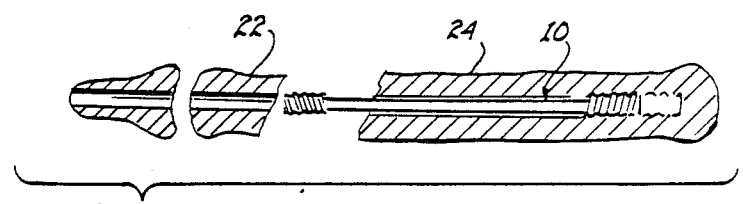
Figure 6:
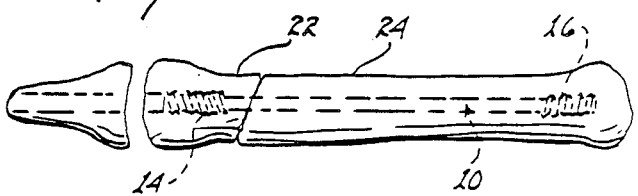

The fractured section 22 and bone 26 are then realigned along the normal axis of the the toe as illustrated in FIG. 4. The proper alignment of the bones in bone sections is aided by extending a tool 30 through the pilot hole 28 which runs through bone 26 and fractured section 22. Tool 30 is engaged with the slot or tool engagement means at the end of screw 10 and the screw is turned in a sense to rotate the screw out of fractured section 24 as shown more fully in FIG. 5. Driving the screw all the way into section 24 is necessary to allow proper alignement of segment 22 without unnecessary traumatizing the muscles (not shown) which surround the bone sections. Once the section 22 has been realigned, screw 10 can be backed out of the section 24 without unduly stretching the muscles. As illustrated in FIG. 5, the bone sections are properly aligned along the correct axis of the bones and the screw is inserted within fractured section 24 and a section of the screw extends outwardly from section 24 toward section 22.

The fractured bone segments 22 and 24 are then completely joined by again rotating screw 10 using tool 30 (not shown in this view) to rotate the screw in the sense which causes threads 16 to advance into the fractured segment 24 while the threads 14 advance into the fractured segment 22. Rotation of the screw is continued until the advancement of the screw into the two fractured segments draws those two segments into proper alignment. During the joining operation, only the threaded sections 14 and 16 make contact with the interior of the bone sections. Smooth shaft 12, being of lesser diameter does not contact the bone sections so that trauma to the bone is minimized. In addition, insertion of the bone screw in the manner described does not require that the bone screw be inserted through bone 26, and does not require the entire length of screw 10 to be driven through fractured section 22.

The joining of the two fractured bone sections, as described above, contemplates that bone screw 10 will be left in place after the fixation of the fracture. The bone screw is rigidly anchored within the bone section and cannot spontaneously work its way out as is often the case when pins are used for aligning the fractured sections.

Thus it is apparent that there has been provided, in accordance with the invention, an improved bone screw and method for joining bone sections using the improved screw which fully meet the objects and advantages set forth above. Although the invention has been described and illustrated with reference to specific embodiments thereof, it is not intended that the invention be limited to these illustrative embodiments. Those skilled in the art will recognize, after review of the foregoing description, that variations and modifications differing from these illustrative embodiments are possible without departing from the spirit of the invention. It is therefore intended that the invention include all such variations and modifications as fall within the scope of the accompanying claims.

What is claimed is:

1. A method for joining fractured sections of a bone which comprises the steps of:

boring a pilot hole along the axis of the fractured phalanx from the end thereof, said pilot hole extending through one of the fractured sections and into the other fractured section;

spreading said fractured sections apart and inserting a bone screw into a first fractured section at the location of the fracture and leaving a portion of said bone screw protruding from an end of said first fractured section at the fracture;

attaching the other fractured section to the protruding portion of said bone screw, said bone screw including opposite handed threads at the ends of a cylindrical shaft having substantially the same diameter at each end and having a screw slot at one end;

aligning said bone screw with said pilot hole;

inserting a tool through said pilot hole from said end of said phalanx to engage said screw slot; and turning said bone screw to advance said screw into each of said fractured sections.

2. The method of claim 1 wherein said step of turning is continued to draw said fractured sections together.

3. The method of claim 1 wherein said step of boring a pilot hole comprises boring a hole having a diameter greater than the diameter of said cylindrical shaft.

4. The method of claim 1 wherein said step of boring a pilot hole comprises boring a single continuous hole through said sections.

5. The method of claim 1 further comprising the step of leaving said bone screw in place after fixation of said fractured sections.

6. The method of claim 1 wherein said step of aligning comprises turning said bone screw in a sense to retract said screw.

* * * * *